United States Patent

Tsuneki et al.

Patent Number: 6,057,470
Date of Patent: May 2, 2000

[54] REACTION DISTILLATION APPARATUS AND REACTION DISTILLATION METHOD

[75] Inventors: Hideaki Tsuneki, Tokyo; Atusi Moriya, Suita; Hiroshi Yoshida, Suita; Hiroki Wakayama, Suita; Kenichi Watanabe, Suita; Yoshiyuki Onda, Suita, all of Japan

[73] Assignee: Nippon Shokubai Co., Ltd., Osaka, Japan

[21] Appl. No.: 09/000,009

[22] PCT Filed: May 20, 1997

[86] PCT No.: PCT/JP97/01685

§ 371 Date: Jan. 21, 1998

§ 102(e) Date: Jan. 21, 1998

[87] PCT Pub. No.: WO97/44108

PCT Pub. Date: Nov. 27, 1997

[30] Foreign Application Priority Data

May 21, 1996 [JP] Japan .................................... 8-126035

[51] Int. Cl.[7] .............................. C07C 68/06; B01J 8/02; B01J 10/00
[52] U.S. Cl. ........................... 558/270; 422/194; 558/274
[58] Field of Search ............................. 422/194; 558/270, 558/274

[56] References Cited

U.S. PATENT DOCUMENTS 5,679,312  10/1997  Jin et al. ............................. 422/194 X

FOREIGN PATENT DOCUMENTS

| 0-461-274-A1 | 12/1991 | European Pat. Off. |
| 52-3923 | 1/1977 | Japan . |
| 59-500671 | 4/1984 | Japan . |
| 4-261142 | 9/1992 | Japan . |
| 7-206781 | 8/1995 | Japan . |

*Primary Examiner*—Michael G. Ambrose
*Attorney, Agent, or Firm*—Nixon & Vanderhye P.C.

[57] ABSTRACT

Reactive distillation equipment applicable to a relatively complicated reaction composed of at least two steps of equilibrium reactions, and a reactive distillation method capable of performing the reaction efficiently. Raw material feeding pipes 5, 6 and 7 are connected to a reactive distillation column 1. The raw material feeding pipes 5, 6 and 7 are disposed on different stages of the reactive distillation column 1 in this order from the top of the column downward. It is preferred that the reactive distillation column 1 includes a stage to which no raw material feeding pipe is connected between a first stage connected to the raw material feeding pipe 5 and a second stage connected to the raw material feeding pipe 6, and between the second stage and a third stage connected to the raw material feeding pipe 7. By feeding raw material (A), raw material (B) and raw material (E) from the raw material feeding pipes 5, 6 and 7, respectively, vapor-liquid contacting of raw materials (A) and (B), and vapor-liquid contacting of product (C) and raw material (E) are carried out.

12 Claims, 1 Drawing Sheet

FIG. 1

REACTION DISTILLATION APPARATUS AND REACTION DISTILLATION METHOD

TECHNICAL FIELD

The present invention relates to reactive distillation equipment and a reactive distillation method applicable to a relatively complicated reaction composed of at least two steps of equilibrium reactions.

BACKGROUND ART

In a conventional art, when the equilibrium of an equilibrium reaction is not biased toward the product system, the reaction efficiency (equilibrium conversion) is improved by biasing the equilibrium toward the product system through reactive distillation. For example, "Chemical Engineering" Vol. 57, No. 1, pages 77–79 (1993) explains the reactive distillation by presenting specific examples.

In general, when performing a relatively complicated reaction composed of at least two steps of equilibrium reactions, reactive distillation is carried out separately for each of the equilibrium reactions. For example, an International Laid-Open Patent Publication, No. WO091/09832, discloses a method of preparing diphenyl carbonates from dimethyl carbonate and phenol through two steps of equilibrium reactions. In this method, one reactive distillation column (reactive distillation equipment) is used for each equilibrium reaction, and therefore two reactive distillation columns are used in total.

However, in this conventional method, during the reactive distillation of the first-step equilibrium reaction for forming methyl phenyl carbonate from dimethyl carbonate and phenol, dimethyl carbonate as a raw material and methanol as a product form an azeotrope. Therefore, the equilibrium is not biased toward the product system, and the equilibrium reaction does not proceeds smoothly. Consequently, carbonate esters are not prepared efficiently. In addition, since two reactive distillation columns are used for the preparation of diphenyl carbonate, a problem arises, i.e., the cost of equipment and utility increases.

Thus, the above-mentioned conventional reactive distillation columns are used only for a relatively simple reaction. In other words, they are not used for a relatively complicated reaction composed of at least two steps of equilibrium reactions. Namely, there is very few known reactive distillation columns which are applicable to consecutive multiple reactions. In such a situation, there is a demand for reactive distillation equipment and reactive distillation methods applicable to a relatively complicated reaction composed of at least two steps of equilibrium reactions.

In order to solve the above-mentioned conventional problem, it is an object of the present invention to provide reactive distillation equipment applicable to a relatively complicated reaction composed of at least two steps of equilibrium reactions, and reactive distillation methods capable of performing such a reaction efficiently.

DISCLOSURE OF THE INVENTION

In order to solve the conventional problem, the present inventors eagerly studied reactive distillation equipment and reactive distillation methods. The inventors found as a result of study that a relatively complicated reaction composed of at least two steps of equilibrium reactions is efficiently carried out through the processes mentioned below using reactive distillation equipment provided with at least a first feed section, a second feed section and a third feed section which are disposed on different plates in this order from the top of a column. Specifically, the relatively complicated reaction is performed efficiently by feeding a raw material (first raw material) having a higher boiling point between two kinds of raw materials provided for the equilibrium reaction from the first feed section and feeding the other raw material (second raw material) having a lower boiling point from the second feed section so as to execute a first equilibrium reaction, and by feeding a third raw material from the third feed section so as to carry out a second equilibrium reaction between the third raw material and a product having a higher boiling point than those of the first and second raw materials between the products produced by the first equilibrium reaction. The present invention was completed based on such a discovery.

Namely, in order to achieve the above-mentioned object, reactive distillation equipment of the present invention is reactive distillation equipment having not less than three stages for performing a reaction composed of at least two steps of equilibrium reactions, and characterized in including at least a first feed section for feeding a raw material (first raw material) having a higher boiling point between two kinds of raw materials provided for the first equilibrium reaction, a second feed section for feeding the other raw material (second raw material) having a lower boiling point, and a third feed section for feeding a third raw material which performs the second equilibrium reaction with a product having a higher boiling point than those of the first and second raw materials between the products produced by the first equilibrium reaction, the first, second and third feed sections being disposed on different stages in this order from the top of a column. Additionally, the reactive distillation equipment of the present invention can include a stage on which no feed section is disposed between two stages provided with feed sections.

According to this structure, in the reactive distillation equipment, the first, second and third feed sections which are fed with different raw materials are disposed on different stages in this order from the top of the column. It is therefore possible to provide reactive distillation equipment applicable to a relatively complicated reaction composed of at least two steps of equilibrium reactions, i.e., a consecutive multiple reaction.

Moreover, reactive distillation equipment including a stage having no feed section between the two stages provided with the feed sections ensures a more efficient consecutive multiple reaction.

In order to achieve the above-mentioned object, a reactive distillation method of the present invention is a reactive distillation method for carrying out a reaction composed of at least two steps of equilibrium reactions using reactive distillation equipment having not less than three stages, and characterized in including the steps of performing a first equilibrium reaction by feeding a raw material (first raw material) having a higher boiling point between two kinds of raw materials provided for the first equilibrium reaction to a first stage and feeding the other raw material (second raw material) having a lower boiling point to a second stage lower than the first stage, and performing a second equilibrium reaction between a third raw material and a product having a higher boiling point than those of the first and second raw materials between the products to be produced by the first equilibrium reaction by feeding the third raw material to a third stage lower than the second stage.

Additionally, in the reactive distillation method of the present invention, a product having a lower boiling point between the products to be produced by the second equilibrium reaction may be the raw material used in the first equilibrium reaction.

In this method, the two kinds of raw materials carry out the first equilibrium reaction, and the third raw material and the product having a higher boiling point between the products produced by the first equilibrium reaction perform the second equilibrium reaction. It is thus possible to provide a method applicable to a relatively complicated reaction composed of at least two steps of equilibrium reactions, i.e., a consecutive multiple reaction.

Moreover, when the product having a lower boiling point between the products produced by the second equilibrium reaction is the raw material used in the first equilibrium reaction, the amount of the raw material participated in the first equilibrium reaction can be reduced. It is thus possible to perform the consecutive multiple reaction more efficiently.

Furthermore, in the reactive distillation method of the present invention, the first equilibrium reaction may be a transesterification between a carboxylate ester represented by formula (1)

$$R^1COOR^2 \quad (1)$$

(wherein each of $R^1$ and $R^2$ independently represents an alkyl group, an alicyclic hydrocarbon group, or an aryl alkyl group) and an aromatic hydroxy compound of formula (2)

$$R^3OH \quad (2)$$

(wherein $R^3$ represents an aromatic group with or without a substituent), and the second equilibrium reaction may be a transesterification between a carboxylate ester represented by formula (3)

$$R^1COOR^3 \quad (3)$$

(wherein $R^1$ represents an alkyl group, an alicyclic hydrocarbon group, or an aryl alkyl group, and $R^3$ is an aromatic group with or without a substituent) and a carbonate ester of formula (4)

$$R^4O\text{—}COOR^5 \quad (4)$$

(wherein each of $R^4$ and $R^5$ independently represents an alkyl group, an alicyclic hydrocarbon group, or an aryl alkyl group).

With the use of the above-mentioned reactive distillation method, it is possible to efficiently prepare carbonate esters represented by $$R^3O\text{—}COOR^6 \quad (5)$$

(wherein $R^3$ represents an aromatic group with or without a substituent, and $R^6$ represents a substituent selected from the group consisting of $R^3$, $R^4$ and $R^5$).

The resultant carbonate esters are industrially effective compounds. For example, diphenyl carbonate as a kind of the carbonate esters is used as a raw material of polycarbonate.

BEST MODE FOR IMPLEMENTING THE INVENTION

The reactive distillation equipment and reactive distillation method of the present invention are applicable to a complex consecutive multiple reaction composed of more than two steps of equilibrium reactions. However, for the sake of explanation, the following description will explain the present invention by presenting an example of the consecutive multiple reaction composed of two steps of equilibrium reactions. More specifically, a product (F) as a target product is produced from raw materials (A), (B) and (E) by performing two steps of equilibrium reactions expressed as:

(first equilibrium reaction)

$$\text{raw material(A)} + \text{raw material(B)} \leftrightarrows \text{product(C)} + \text{product(D)}$$

and (second equilibrium reaction)

$$\text{product(C)} + \text{raw material(E)} \leftrightarrows \text{product(F)} + \text{product(G)}.$$

These equilibrium reactions need to satisfy such conditions that the relationship among the boiling points of raw material (A) as the first raw material, raw material (B), and raw material (E) as the third material is $$\text{raw material (A)} > \text{raw material (B)} > \text{raw material (E)},$$

the relationship between the boiling points of product (C) and product (D) is $$\text{product (C)} > \text{product (D)},$$

and the relationship between the boiling points of product (F) and product (G) is $$\text{product (F)} > \text{product (G)}.$$

In the following description, the first equilibrium reaction is referred to as the "first-step reaction", and the second equilibrium reaction is called the "second-step reaction".

Figure 1:
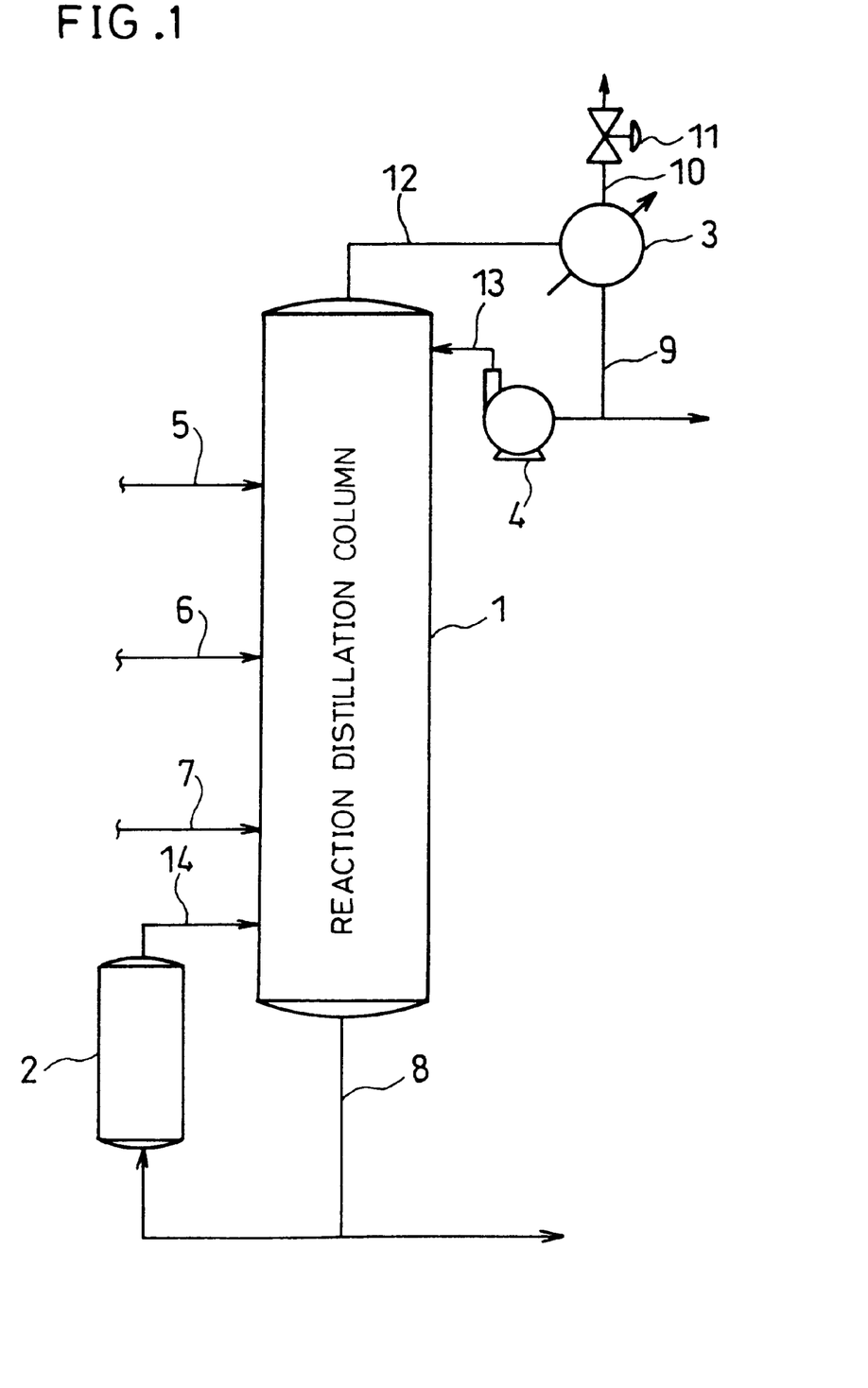
FIG. 1 is a block diagram showing a schematic structure of reactive distillation equipment according to one embodiment of the present invention.

Referring now to FIG. 1, the following description will explain an embodiment of the present invention. As illustrated in FIG. 1, reactive distillation equipment 1 (hereinafter referred to as the "reactive distillation column") of the present invention is provided with a reboiler 2, condenser 3, a pump 4, etc.

The reactive distillation column 1 has not less than three stages, and ensures vapor-liquid contacting between the raw material (A) and raw material (B) and between the product (C) and raw material (E). The reactive distillation column 1 is connected to raw material feeding pipes 5, 6 and 7. The reboiler 2 is connected to the bottom of the reactive distillation column 1 through a extracting pipe 8 and a conduit 14. The condenser 3 is connected to the top of the reactive distillation column 1 through a conduit 12.

The raw material feeding pipes 5, 6 and 7 are disposed on different stages in this order from the top of the reactive distillation column 1 downward. More specifically, the raw material feeding pipe 6 is connected to a stage which is lower than a stage to which the raw material feeding pipe 5 is connected, and the raw material feeding pipe 7 is connected to a stage which is lower than the stage to which the raw material feeding pipe 6 is connected.

It is preferred that the reactive distillation column 1 additionally includes a stage to which no raw material feeding pipe is connected between the stage (first stage) to which the raw material feeding pipe 5 is connected and the stage (second stage) to which the raw material feeding pipe 6 is connected and between the second stage and the stage (third stage) to which the raw material feeding pipe 7 is connected. The raw material feeding pipe 7 may be connected to the bottom of the reactive distillation column 1.

The raw material feeding pipe 5 functioning as a first feed section continuously feeds the raw material (A) to the reactive distillation column 1. The raw material feeding pipe 6 as a second feed section continuously feeds the raw material (B) to the reactive distillation column 1. The raw material feeding pipe 7 as a third feed section continuously feeds the raw material (E) to the reactive distillation column 1.

The reboiler 2 is connected to the bottom of the reactive distillation column 1 through the extracting pipe 8 and the conduit 14. The reboiler 2 heats the bottom liquid that has been drawn out through the extracting pipe 8, and feeds the heated liquid back to the bottom of the reactive distillation column 1 through the conduit 14. Namely, the reboiler 2 circulates the bottom liquid by heating. The extracting pipe 8 branches so that a part of the bottom liquid is continuously drawn out as a residue from the reaction system.

The condenser 3 condenses the distillate of the reactive distillation column 1 into a liquid phase. The condenser 3 is connected to the top of the reactive distillation column 1 through the conduit 12, and connected to the pump 4 through a extracting pipe 9. The condenser 3 includes a regulating pipe 10 provided with a pressure control valve 11. The extracting pipe 9 branches so that a part of the distillate is continuously removed from the reaction system.

The pump 4 refluxes the distillate to the reactive distillation column 1 at a predetermined reflux ratio. The pump 4 is connected to the condenser 3 through the extracting pipe 9, and connected to the top of the reactive distillation column 1 through a conduit 13.

Next, an example of the process for preparing product (F) using the reactive distillation equipment having the above-mentioned structure is explained below. First, the raw materials (A), (B) and (E) are continuously fed to the reactive distillation column 1 through the raw material feeding pipes, 5, 6 and 7, respectively. The raw materials (A), (B) and (E) may be fed in liquid phase, gaseous phase, or vapor-liquid-mixed phase. In addition, the raw material (A) may contain a part of the raw material (B), or the raw material (B) may contain a part of the raw material (A).

Subsequently, the raw materials (A) and (B) fed to the reactive distillation column 1 are subjected to vapor-liquid contacting, i.e., reacted and distilled. As a result, the first-step reaction proceeds, and the products (C) and (D) are produced and then separated. The product (C) flows downward in the reactive distillation column 1. Moreover, the product (D) as a by-product is removed continuously as a distillate.

Next, the product (C) and the raw material (E) are subjected to vapor-liquid contacting, i.e., reacted and distilled. As a result, the second-step reaction proceeds, and the products (F) and (G) are produced and then separated. The product (G) as a by-product flows upward in the reactive distillation column 1, and is removed continuously as a distillate. Additionally, when the product (G) is the raw material used in the first-step reaction, i.e., when the product (G) is identical with the raw material (B), the product (G) is reacted in the first-step reaction.

On the other hand, the product (F) as a target product is continuously drawn out as a residue (bottom liquid) from the reaction system, i.e., from the reactive distillation column 1. In short, the product (F) is continuously removed as a residue from the reaction system.

By performing the above-mentioned reactions, it is possible to efficiently prepare the product (F) continuously. When the product (G) is used in the first-step reaction, the kinds of compounds which are present in the reactive distillation column 1 decreases, and therefore the reaction system is simplified. Moreover, since the amount of the raw material (B) fed through the raw material feeding pipe 6 can be reduced, it is possible to perform the above-mentioned consecutive multiple reaction more efficiently.

Furthermore, for example, when a homogeneous catalyst is used for the first-step reaction and/or the second-step reaction, the catalyst is continuously fed to the reactive distillation column 1 together with the raw material (A) and/or the raw material (B). The catalyst can be separated/collected from the product (F) using a known method such as distillation.

On the other hand, for example, when a heterogeneous catalyst is used for the first-step reaction and/or the second-step reaction, the catalyst is retained in the reactive distillation column 1. Additionally, when a packed column (to be described later) is used as the reactive distillation column 1, it is possible to entirely or partially replace the material packed in the reactive distillation column 1 with the heterogeneous catalyst, and pack the reactive distillation column 1 with the heterogeneous catalyst. When a plate column (to be described later) is used as the reactive distillation column 1, the heterogeneous catalyst can be retained in the plate or downcomer. In the case where the heterogeneous catalyst is used, the catalyst used in the first-step reaction and the catalyst used in the second-step reaction can be the same or different from each other.

Moreover, for example, when a solvent is used in the first-step reaction and/or the second-step reaction, it is necessary to additionally provide the reactive distillation column with a solvent feeding pipe (not shown), and continuously feed the solvent through the solvent feeding pipe.

The reactive distillation column 1 needs to have a structure in which a vapor phase section is provided in the reactive distillation column 1 and a produced low-boiling point component is continuously separated and removed to the vapor phase section, i.e., a structure capable of carrying out so-called reactive distillation. As the reactive distillation column 1, a continuous multi-stage distillation column is suitable.

As the continuous multi-stage distillation column, it is preferred to use a distillation column having not less than three stages in addition to the top stage and the bottom stage. As the distillation column, it is possible to employ generally-used distillation columns, for example, packed columns packed with various packings, such as Raschig ring, Pall ring, Intelox saddle, Dixon packing, McMahon packing, and Sulzer packing; and plate columns using trays (plates), such as a bubble cap tray, sieve tray, and valve tray. It is also possible to use a composite distillation column having both plates and a packing bed. The number of stages means the number of plates in a plate column or the theoretical number of stages in a packed column.

There is no need to restrict the structure of the reactive distillation equipment to the one shown in FIG. 1. The reactive distillation equipment and the reactive distillation method of the present invention can be applied to a complex consecutive composition reaction composed of more than two steps of equilibrium reactions as well as to a consecutive multiple reaction composed of two steps of equilibrium reactions. In this case, it is necessary to provide the reactive distillation column with a number of the raw material feeding pipes equal to the number of kinds of the raw materials.

The following description will explain in detail the reactive distillation equipment and the reactive distillation method of the present invention by presenting specific examples. For instance, in the explanation presented below, the first-step reaction is a transesterification between a carboxylate ester represented by formula (1)

$$R^1COOR^2 \tag{1}$$

(wherein each of $R^1$ and $R^2$ independently represents an alkyl group, an alicyclic hydrocarbon group, or an aryl alkyl group) and an aromatic hydroxy compound of formula (2)

$$R^3OH \tag{2}$$

(wherein $R^3$ represents an aromatic group with or without a substituent), and the second-step reaction is a transesterification between a carboxylate ester represented by formula (3)

$$R^1COOR^3 \tag{3}$$

(wherein $R^1$ represents an alkyl group, an alicyclic hydrocarbon group, or an aryl alkyl group, and $R^3$ is an aromatic group with or without a substituent) and a carbonate ester of formula (4)

$$R^4O\text{—}COOR^5 \tag{4}$$

(wherein each of $R^4$ and $R^5$ independently represents an alkyl group, an alicyclic hydrocarbon group, or an aryl alkyl group).

Therefore, one of the carboxylate ester represented by formula (1) and the aromatic hydroxy compound of formula (2) corresponds to the raw material (A), and the other corresponds to the raw material (B). In addition, the carboxylate ester represented by formula (3) corresponds to the product (C), and the carbonate of formula (4) corresponds to the raw material (E).

The above-mentioned reaction produces a carbonate ester represented by formula (5)

$$R^3O\text{—}COOR^6 \tag{5}$$

(wherein $R^3$ represents an aromatic group with or without a substituent, and $R^6$ represents a substituent selected from the group consisting of $R^3$, $R^4$ and $R^5$). Namely, the carbonate ester of formula (5) corresponds to the product (F).

In the following explanation, among the carbonate esters represented by formula (5), carbonate esters (5) wherein the substituent represented by $R^6$ is the substituent $R^4$ or $R^5$ are called carbonate monoesters, and carbonate esters (5) wherein the substituent represented by $R^6$ are the substituent $R^3$ are referred to as carbonate diesters.

The above-mentioned second-step reaction includes two stages. Namely, a reaction for generating a carbonate monoester proceeds in one stage, and a reaction for generating a carbonate diester is carried out in the other stage.

More specifically, first, a transesterification of the substituent $R^3$ of a carboxylate ester represented by formula (3) (hereinafter referred to as the carboxylate ester (3)) with either the substituent $R^4$ or $R^5$ of the carbonate ester represented by formula (4) (hereinafter referred to as the carbonate ester (4)) is performed. As a result, a carbonate monoester is produced, and a carboxylate ester represented by formula (6)

$$R^1COOR^7 \tag{6}$$

(wherein $R^1$ represents an alkyl group, alicyclic hydrocarbon group, or aryl alkyl group, and $R^7$ represents a substituent selected from the group consisting of $R^4$ and $R^5$) is formed as a by-product (hereinafter referred to as the carboxylate ester (6)).

Next, a transesterification of the remaining substituent $R^4$ ($R^5$) of the carbonate monoester with the substituent $R^3$ of the carboxylate ester (3) is carried out. As a result, carbonate diester is produced, and the carboxylate ester (6) is by-produced. The carboxylate ester (6) corresponds to the product (G).

The carboxylate ester represented by above-mentioned formula (1) (hereinafter referred to as the carboxylate ester (1)) is not limited as long as it is a compound wherein substituents represented by $R^1$ and $R^2$ in formula (1) are independently selected from the group consisting of an alkyl, an alicyclic hydrocarbon group, and an aryl alkyl group. It is desirable to use an alkyl group of 1 to 10 carbons, an alicyclic hydrocarbon group of 3 to 10 carbons, and an aryl alkyl group of 7 to 10 carbons.

More specifically, examples of the carboxylate ester (1) include methyl acetate, ethyl acetate, propyl acetate, butyl acetate, cyclohexyl acetate, benzyl acetate, 2-ethylhexyl acetate, methyl propionate, ethyl propionate, propyl propionate, butyl propionate, methyl butyrate, ethyl butyrate, propyl butyrate, methyl isobutyrate, ethyl isobutyrate, propyl isobutyrate, methyl valerate, ethyl valerate, propyl valerate, methyl isovalerate, ethyl isovalerate, propyl isovalerate, methyl hexanoate, ethyl hexanoate, propyl hexanoate, methyl heptanoate, and ethyl heptanoate.

The carboxylate ester (6) is preferably reusable as the carboxylate ester (1). It is therefore desirable that the substituent $R^2$ of the carboxylate ester (1) and the substituents $R^4$ and $R^5$ of the carbonate ester (4) are equal to each other.

It is also desirable to select the substituents $R^2$, $R^4$ and $R^5$ so that the carboxylate ester (6) and a by-produced alcohol (to be described later) do not form an azeotrope. By satisfying these conditions, the carboxylate ester (6) can be easily separated and collected. When the carboxylate ester (6) is entirely reusable as the carboxylate ester (1), the carboxylate ester (1) is not substantially consumed.

In order to improve the reaction efficiency (equilibrium conversion) by biasing the equilibrium of the transesterification reaction toward the product system, it is desirable to remove from the reaction system an alcohol which is formed as a by-product by the first-step reaction and represented by formula (7)

$$R^2OH \tag{7}$$

(wherein $R^2$ represents an alkyl group, an alicyclic hydrocarbon group, or an aryl alkyl group). Therefore, among the above-mentioned compounds, carboxylate ester (1) whose boiling point is higher than the boiling point of the by-produced alcohol is more preferred. The alcohol represented by formula (7) corresponds to the product (D).

In order to further improve the reaction efficiency of the first-step reaction, it is desirable to use carboxylate ester (1) which does not form an azeotrope with the alcohol represented by formula (7) (hereinafter just referred to as the alcohol). Examples of such a carboxylate ester (1) are compounds including an acyl group having more than 3 carbons, such as ethyl butyrate, butyl butyrate, isovalerate, valerate and hexanoate (or compounds in which the substituent $R^1$ has more than 2 carbons). When carboxylate ester (1) satisfying these conditions is used, it is logically possible to substantially completely convert carboxylate ester (1) to carboxylate ester (3).

The aromatic hydroxy compound represented by above-mentioned formula (2) is not limited as long as it is a compound whose substituent represented by $R^3$ is an aromatic group. The aromatic group may have a substituent.

More specifically, the aromatic hydroxy compound is, for example, phenol, o-cresol, m-cresol, p-cresol, o-chlorophenol, m-chlorophenol, p-chlorophenol, o-ethylphenol, m-ethylphenol, p-ethylphenol, o-isopropylphenol, m-isopropylphenol, p-isopropylphenol, o-methoxyphenol, m-methoxyphenol, p-methoxyphenol, xylenols, α-naphthol, or β-naphthol. These aromatic hydroxy compounds may be suitably mixed for use. Among the listed compounds, phenol is suitable for industrial use.

In order to improve the equilibrium conversion of the aromatic hydroxy compound, it is desirable to use carboxylate ester (1) whose boiling point is lower than that of carboxylate ester (3) to be produced. With respect to the combination of such carboxylate ester (1) and aromatic hydroxy compound, any combinations can achieve improved equilibrium conversion except a combination of 2-ethylhexyl acetate and phenol and a combination of benzyl acetate and phenol.

When the carboxylate ester (1) is an acetate forming an alcohol of less than 8 carbons or a propionate forming an alcohol of less than 9 carbons, it is possible to use the carboxylate ester (1) along with any of the above-mentioned aromatic hydroxy compounds. The carboxylate ester (1) and the carboxylate ester (3) are allowed to form an azeotrope.

More specifically, examples of the carboxylate ester (3) obtained by the above-mentioned first-step reaction are phenyl acetate, isomers of methyl phenylacetate, isomers of ethyl phenylacetate, isomers of chlorophenyl acetate, isomers of isopropylphenyl acetate, isomers of methoxyphenyl acetate, isomers of dimethylphenyl acetate, isomers of naphthyl acetate, isomers of methylphenyl propionate, phenyl butyrate, phenyl isobutyrate, phenyl valerate, isomers of methylphenyl valerate, phenyl isovalerate, phenyl hexanoate, and phenyl heptanoate.

The carbonate ester (4) is not particularly limited as long as it is a compound wherein each of the substituents $R^4$ and $R^5$ in formula (4) is independently represents an alkyl group, an alicyclic hydrocarbon group, and an aryl alkyl group. It is desirable to use an alkyl group of 1 to 10 carbons, an alicyclic hydrocarbon group of 3 to 10 carbons, and an aryl alkyl group of 7 to 10 carbons.

More specifically, examples of the carbonate ester (4) include dimethyl carbonate, diethyl carbonate, di-n-propyl carbonate, diisopropyl carbonate, isomers of dibutyl carbonate, isomers of dipentyl carbonate, isomers of dihexyl carbonate, isomers of diheptyl carbonate, isomers of dioctyl carbonate, isomers of dinonyl carbonate, isomers of didecyl carbonate, dicyclohexyl carbonate, dibenzyl carbonate, isomers of diphenethyl carbonate, or isomers of di(methylbenzyl) carbonate. These carbonate esters (4) may be suitably mixed for use. Among the listed compounds, dimethyl carbonate is suitable for industrial use.

In order to improve the reaction efficiency (the equilibrium conversion) by biasing the equilibrium of the transesterification reaction toward the product system, it is desirable to use carboxylate ester (3) whose boiling point is higher than the boiling point of the carboxylate ester (6) among the above-listed compounds. An example of the combination of the carboxylate ester (3) and the carbonate ester (4) is a carboxylate ester (3) wherein the substituent $R^3$ is a phenyl group and a compound having less than 8 carbons when the substituents $R^4$ and $R^5$ of carbonate ester (4) form a straight chain.

Moreover, in order to continuously remove the produced carbonate ester (5) from the reaction system, it is desirable to use carboxylate ester (3) whose boiling point is lower than the boiling point of the carbonate ester (5). An example of the carboxylate ester (3) is a compound having less than 8 carbons when the substituent $R^1$ forms a straight chain.

Additionally, in order to facilitate the separation of the produced carbonate ester (5) and the carboxylate ester (3), a relatively large difference in boiling point between the carboxylate ester (3) and the carbonate ester (5) is preferred. Meanwhile, in order to improve the equilibrium conversion of the carbonate ester (4), it is desired that the difference in boiling point between the carboxylate ester (3) and the carbonate ester (4) is relatively small and the difference in boiling point between the carboxylate ester (3) and the carboxylate ester (6) is relatively large.

The first-step reaction is an equilibrium reaction (equilibrium constant $K=10^{-3}$ to $10^{-4}$) in which the equilibrium is extremely biased toward the original system. Therefore, in order to improve the reaction efficiency (equilibrium conversion) by biasing the equilibrium of the transesterification reaction toward the product system, it is desirable to continuously extract an alcohol from the reaction system. Moreover, when distilling off the alcohol, it is desirable to sufficiently separate the alcohol from the carboxylate ester (1).

The second-step reaction is also an equilibrium reaction (equilibrium constant $K=10^{-1}$ to $10^1$), but the equilibrium of the transesterification reaction is not as much as biased toward the original system as compared to the first-step reaction. Therefore, the second-step reaction proceeds more easily compared to the first-step reaction. However, similarly to the first-step reaction, in order to improve the reaction efficiency (equilibrium conversion) by biasing the equilibrium of the transesterification reaction toward the product system, it is desirable to continuously remove the carboxylate ester (6) from the reaction system.

Moreover, when distilling off the carboxylate ester (6), it is desirable to sufficiently separate the carboxylate ester (6) from the carboxylate ester (3). However, when the carboxylate ester (6) and the carboxylate ester (1) are the same compound, it is not necessary to remove the carboxylate ester (6) from the reaction system.

In the above-mentioned process for preparing the carbonate ester (5), a transesterification between the carboxylate ester (1) and an aromatic hydroxy compound is carried out under the presence of a catalyst (first-step reaction). In addition, a transesterification between the carboxylate ester (3) and the carbonate ester (4) is performed under the presence of a catalyst (second-step reaction). The catalyst used for the first-step reaction and the catalyst used for the second-step reaction may be the same or different from each other.

Examples of the catalysts are: mineral acids such as sulfuric acid; sulfonic acids such as paratoluenesulfonic acid; solid acids such as ion exchange resins and zeolite; base such as sodium hydroxide; metal alkoxide such as tetraisopropoxide titanate, and zirconium(IV) isopropoxide; Lewis acid such as aluminum chloride and titanium tetrachloride, and compounds producing Lewis acid; metal phenoxides such as lead phenoxide and phenoxytitanium; lead oxides; lead salts such as lead carbonates; metal acetylacetonate complex such as zirconium(IV) acetylacetonate, copper (II) bis(acetylacetonate), zinc(II) acetylacetonate and lithium acetylacetonate; organotin compounds such as dibutyltin oxide; titanium silicate; and metal-substituted aluminum phosphate. It is also possible to use typical proton acid, proton base, solid acid and solid base as catalysts. Among the listed catalysts, metal alkoxide, Lewis acid, compounds producing Lewis acid, metal phenoxides, organotin compounds, titanium silicate, and metal-substituted aluminum phosphate are particularly preferred.

When using a homogeneous catalyst, a mixed solution containing the catalyst is fed to the reactive distillation column 1. It is possible to feed the catalyst by mixing it with at least one of the carboxylate ester (1), the carbonate ester (4) and an aromatic hydroxy compound. In this case, it is also possible to feed the mixed solution containing the catalyst to a stage to which the carboxylate ester (1), the carbonate ester (4) or the aromatic hydroxy compound is fed, or to a different stage. In the reactive distillation column 1, when the number of regions (stages) in which the catalyst is present is increased, the contact frequency of the reaction liquid and the catalyst increases, thereby achieving good reaction efficiency. It is therefore desirable to feed the catalyst to a stage as high as possible in the reactive distillation column 1.

When the homogeneous catalyst is used, the minimum catalyst concentration is 0.1 ppm, preferably 1 ppm, and more preferably 10 ppm, based on the total amount of carboxylate ester (1) and the aromatic hydroxy compound. The maximum catalyst concentration up to which the catalyst dissolves in a saturated state in the reaction liquid in the reactive distillation column 1 is about 10 weight percent, preferably 5 weight percent, and more preferably 1 weight percent.

When the heterogeneous catalyst is used, the minimum amount of the catalyst is 0.1 weight percent, preferably 0.5 weight percent, and more preferably 1 weight percent based on the total amount of carboxylate ester (1) and the aromatic hydroxy compound. In this case, the maximum amount of the catalyst is 40 weight percent, preferably 30 weight percent, and more preferably 20 weight percent.

The method for feeding the raw materials to the reactive distillation column 1 is not particularly limited. Therefore, it is possible to feed the carboxylate ester (1), aromatic hydroxy compound and carbonate ester (4) in liquid form, gaseous form, or vapor-liquid mixed form. The carboxylate ester (1) may contain a part of the aromatic hydroxy compound, and the aromatic hydroxy compound may contain a part of the carboxylate ester (1).

Although the mole ratio of the carboxylate ester (1) and the aromatic hydroxy compound in the first-step reaction is varied depending on the type and amount of a catalyst to be used and the reaction conditions, it is preferably in a range of from 1:50 to 50:1, more preferably in a range of from 1:20 to 20:1, and most preferably in a range of from 1:5 to 5:1. As described above, the first-step reaction is an equilibrium reaction which is extremely biased toward the original system. Therefore, by using one of the carboxylate ester (1) and the aromatic hydroxy compound excessively, the reaction efficiency (equilibrium conversion) of the other can be increased. However, if the mole ratio thereof is out of the above-mentioned ranges, the excessively used carboxylate ester (1) or aromatic hydroxy compound needs to be collected and recycled. Thus, this method is industrially disadvantageous and undesirable.

In the second-step reaction, the mole ratio of the carboxylate ester (3) and the carbonate ester (4) is varied depending on the type and amount of a catalyst to be used, but it is preferably in a range of from 1:50 to 50:1, more preferably in a range of from 1:20 to 20:1, and most preferably in a range of from 1:5 to 5:1. By using one of the carboxylate ester (3) and the carbonate ester (4) excessively, the reaction efficiency (equilibrium conversion) of the other can be increased. However, if the mole ratio thereof is out of the above-mentioned ranges, the excessively used carboxylate ester (3) or carbonate ester (4) needs to be collected and recycled. Thus, this method is industrially disadvantageous and undesirable.

In the second-step reaction, the reaction system may include the carboxylate ester (1) and the aromatic hydroxy compound as unreacted compounds which was not reacted in the first-step reaction. In order to efficiently produce the carbonate ester (5), the content of the carboxylate ester (3) in the total amount of the carboxylate ester (3), carboxylate ester (1) and aromatic hydroxyl compound is preferably not lower than 10 mole percent, more preferably not lower than 20 mole percent, and still more preferably not lower than 30 mole percent.

When operating the reactive distillation column 1, factors determining the operating conditions are, for example, the number of plates, the operating temperature (reaction temperature), the operating pressure, the residence time of liquid, the reflux ratio, the amount of hold-up liquid.

Namely, when performing the first equilibrium reaction, the temperature and pressure are adjusted so that a product having higher boiling points than the first and second raw materials between the products to be produced by the first equilibrium reaction are separated from the first and second raw materials based on the differences in boiling point.

Moreover, when performing the first equilibrium reaction, the temperature and pressure are adjusted so that products having lower boiling points than the first and second raw materials between the products to be produced by the first equilibrium reaction are separated based on the differences in boiling point, and the first equilibrium reaction is promoted.

When performing the second equilibrium reaction, the temperature and pressure are adjusted so that a product having s higher boiling point between the products to be produced by the second equilibrium reaction is removed as a target product from the reaction separator based on the differences in boiling point.

In addition, when performing the second equilibrium reaction, the temperature and pressure are adjusted so that a product having a lower boiling point between the products to be produced by the second equilibrium reaction is separated from the second equilibrium reaction system based on the differences in boiling point, and the second equilibrium reaction is promoted.

More specifically, although the operating temperature varies depending on the types of the carboxylate ester (1), aromatic hydroxy compound and carbonate ester (4), the type and amount of the catalyst, and other conditions (factors), the minimum operating temperature is 100° C., preferably 140° C., and more preferably 160° C. The maximum operating temperature is 350° C., and preferably 300° C.

When the operating temperature is lower than 100° C., since the catalytic activity decreases, the reaction time becomes longer and the productivity is lowered. Thus, an operating temperature lower than 100° C. is not preferred. On the other hand, an operating temperature higher than 350° C. is not preferred because side reactions such as the production of ethers (such as diaryl ethers and alkyl aryl ethers) are likely to occur due to a dehydrating reaction, or a decarbonating reaction. Furthermore, the pressure inside the reactive distillation column 1 excessively increases.

More specifically, the operating pressure is a reduced pressure, normal pressure or increased pressure. Although the operating pressure varies depending on the types of the carboxylate ester (1), aromatic hydroxy compound and carbonate ester (4), the type and amount of the catalyst, and other conditions (factors), the lower limit is 100 mmHg, preferably 500 mmHg, and more preferably 760 mmHg (normal pressure). The upper limit is 100 Kg/cm$^2$, preferably 50 Kg/cm$^2$, and more preferably 10 Kg/cm$^2$.

The amount of hold-up liquid and the number of plates are closely related to the reaction time, i.e., the residence time. Namely, in order to improve the equilibrium conversion, it is necessary to increase the residence time to a degree. Moreover, in order to increase the residence time, it is necessary to increase the amount of hold-up liquid or the number of plates. Although an increase in the amount of hold-up liquid is preferred, if the amount of hold-up liquid becomes larger than a certain value, flooding occurs. Therefore, the amount of hold-up liquid with respect to the capacity (volume) of an empty column of the reactive distillation column 1, i.e., the volume ratio of the hold-up liquid to the empty column, is preferably in a range of from 0.005 to 0.75, and more preferably in a range of from 0.01 to 0.5. In the case where the number of plates is increased, considering the manufacturing cost of the reactive distillation column 1, the height restriction and the costs of utility and installation, a preferred number of plates is approximately between 5 and 100.

When the number of plates is increased, if the difference in boiling point between the carboxylate ester (1) and the alcohol is relatively small in the first-step reaction, and if the difference in boiling point between the carboxylate ester (3) and the carbonate monoester or the carboxylate ester (6) is relatively small in the second-step reaction, the vapor-liquid separation efficiency is improved.

In the first-step reaction, the reflux ratio is preferably in a range of from 0 to 100, more preferably in a range of from 0 to 50, and still more preferably in a range of from 0 to 25. When the carboxylate ester (1) and the alcohol form an azeotrope in the first-step reaction, the reflux ratio is preferably made zero or a relatively small value. When the difference in boiling point between the carboxylate ester (1) and the alcohol is relatively small, the reflux ratio is preferably made a relatively large value by considering the costs of utility and installation.

When a heterogeneous catalyst is used, if the catalyst is retained in the reactive distillation column, it is not necessary to separate the catalyst. Even when the catalyst is used in the form of slurry, the heterogeneous catalyst can be easily removed and collected from the reaction liquid after the completion of the reaction by using known methods, for example, a centrifugal method or filtration.

On the other hand, when a homogeneous catalyst is used, the homogeneous catalyst can be easily separated and collected from the reaction liquid after the completion of the reaction by using a known method, for example, distillation.

By separating the catalyst after the completion of the reaction using the above-mentioned method, and then by using known methods such as distillation, extraction and recrystallization, the carbonate ester (5), i.e., carbonate diester, as a target product can be easily isolated. Moreover, the carboxylate ester (6) and carbonate monoester as by-products, or carbonate ester (4) and the aromatic hydroxy compound, etc. as unreacted compounds can be easily separated and collected, if necessary.

In the process for preparing carbonate ester (5), a solvent can be added to the reaction system, i.e., the reaction liquid, if necessary. As for a solvent to be added for facilitating the reaction operation, compounds inert to the reaction system are used. Examples of such compounds are ethers, aliphatic hydrocarbon, aromatic hydrocarbon, and halogenated hydrocarbon.

When carboxylate ester (1) and the alcohol form an azeotrope, it is preferred that a solvent, which forms an azeotrope whose azeotropic point is lower than that of the above-mentioned azeotrope with the alcohol, is present in the reaction system. For example, when the alcohol is methanol, preferred solvents are compounds such as benzene and cyclohexane.

The solvent forms an azeotrope of a relatively low azeotropic boiling point with methanol. Since the formation of an azeotrope between the carboxylate ester (1) and methanol is controlled, the carboxylate ester (1) and methanol are easily separated, thereby improving the equilibrium conversion. Moreover, even when the carboxylate ester (1) and methanol do not form an azeotrope, in order to facilitate the separation thereof, a solvent which forms an azeotrope of a low azeotropic point with the alcohol can be made present in the reaction system.

In order to easily remove the alcohol and the carboxylate ester (6) from the reaction system, an inert gas (nitrogen gas) can be introduced to the reaction system from the lower part of the reactive distillation column 1.

Next, the following description will explain an example of the method for preparing the carbonate ester (5). First, an aromatic hydroxy compound, carboxylate ester (1), and carbonate ester (4) are continuously fed to the reactive distillation column 1 through the raw material feeding pipes, 5, 6 and 7, respectively.

As a result, the aromatic hydroxy compound and carboxylate ester (1) fed to the reactive distillation column 1 are subjected to vapor-liquid contacting, i.e., reacted and distilled. Consequently, the first-step reaction proceeds, the carboxylate ester (3) and alcohol are produced and then separated. The carboxylate ester (3) flows downward in the reactive distillation column 1. Moreover, the alcohol as a by-product is continuously removed as a distillate.

Next, the carboxylate ester (3) and the carbonate ester (4) are subjected to vapor-liquid contacting, i.e., reacted and distilled. As a result, the second-step reaction proceeds, the carbonate ester (5) and carboxylate ester (6) are produced and then separated. The carboxylate ester (6) as a by-product flows upward in the reactive distillation column 1, and is continuously removed as a distillate. When the carboxylate ester (6) and carbonate ester (1) are the same compound, the carboxylate ester (6) is used in the first-step reaction.

Meanwhile, the carbonate ester (5) as a target product is continuously drawn out as a residue (bottom liquid) from the reaction system, i.e., from the reactive distillation column 1. In short, the carbonate ester (5) is continuously removed as a residue from the reaction system.

By performing the above-mentioned reactions, it is possible to efficiently prepare the carbonate ester (5) continuously. When the carboxylate ester (6) is used in the first-step reaction, the kinds of compounds which are present in the reactive distillation column 1 decreases, and therefore the reaction system is simplified. Moreover, since the amount of the carboxylate ester (1) fed through the raw material feeding pipe 6 can be reduced, it is possible to perform the above-mentioned consecutive multiple reaction more efficiently.

The present invention will be described in detail below by presenting examples which should not be considered as limiting, in any way, the scope of the invention. The term "percent" used in the examples means "percent by weight".

[EXAMPLE 1]

A consecutive multiple reaction composed of a combination of two steps of equilibrium reactions was carried out using reactive distillation equipment shown in FIG. 1. In this case, a column formed by connecting a stainless distillation column to the top of stainless plate column was used as the reactive distillation column 1.

The plate column had an inner diameter of 20 mm, and 60 plates. The raw material feeding pipe 5 was connected to the top of the topmost (60th) plate, i.e., the top of the column, the raw material feeding pipe 6 was connected to the 20th plate, and the raw material feeding pipe 7 was connected to the bottom of the lowest (first) plate, i.e., the bottom of the column. Thus, the plate column functioned as a reactor section.

The distillation column had a height of 1 m and an inner diameter of 20 mm, and was packed with a 1.5 mm$\phi$ stainless Dixon packing as a packing material. Therefore, the distillation column served as a condenser section. Heat necessary for distillation was fed by heating the bottom of the plate column with a heater instead of heating the bottom liquid using, for example, the reboiler 2. The operating conditions for the reactive distillation column 1 were a column bottom temperature of 240° C., and a column top pressure (gage pressure) of 3.4 kg/cm$^2$. The reflux operation was not performed, but slight internal reflux occurred because a part of the distillate condensed in the distillation column due to radiation of heat.

A raw material liquid made of phenol as the raw material (A) and titanium tetraphenoxide "Ti(OPh)$_4$" as the catalyst was continuously fed to the reactive distillation column 1 through the raw material feeding pipe 5. The amount of raw material liquid fed per hour was 60 grams. Additionally, a methyl valerate as the raw material (B) which was partly in gaseous form was continuously fed to the reactive distillation column 1 through the raw material feeding pipe 6. The amount of methyl valerate fed per hour was 128 grams. The titanium tetraphenoxide was added so that the amount of titanium was 500 ppm based on the raw material (the total amount of methyl valerate and phenol). Furthermore, dimethyl carbonate as the raw material (E) was fed in gaseous form continuously to the reactive distillation column 1 through the raw material feeding pipe 7. The amount of dimethyl carbonate fed per hour was 18.6 grams.

Vapor-liquid contacting (first-step reaction) was carried out while performing a transesterification between the methyl valerate and phenol in the reactive distillation column 1. Vapor-liquid contacting (second-step reaction) was carried out while performing a transesterification between the produced phenyl valerate (product (C)) and dimethyl carbonate. Then, a residue containing the produced methylphenyl carbonate and diphenyl carbonate (products (F)) was continuously removed from the reaction system through the extracting pipe 8. The amount of the residue drawn out per hour was 93.3 grams. Moreover, the distillate containing the by-produced methanol (product (D)) was continuously removed from the reaction system through the extracting pipe 9. The amount of the distillate drawn out per hour was 111 grams.

The composition of the residue was analyzed. The residue was composed of 25.6 percent of phenyl valerate, 17.3 percent of methylphenyl carbonate, 14.0 percent of diphenyl carbonate, 4.5 percent of dimethyl carbonate, 12.3 percent of methyl valerate, and 26.2 percent of phenol. The conversion of phenol was 59.6 percent, and the conversion of dimethyl carbonate was 75.5 percent.

The composition of the distillate was analyzed. The distillate contained very little dimethyl carbonate. The reaction liquid which was present on the 13th plate from the bottom of the plate column was extracted and analyzed. The reaction liquid contained very little dimethyl carbonate. The methyl valerate (product (G)) by-produced in the second-step reaction was placed as the raw material (B) for the first-step reaction.

[EXAMPLE 2]

A consecutive multiple reaction was carried out using the same reactive distillation equipment as that used in Example 1, under the same reaction conditions as those in Example 1, except that the amount of methyl valerate fed per hour was changed to 124 grams from 128 grams of Example 1 and the amount of dimethyl carbonate fed per hour was changed to 24.4 grams from 18.6 grams.

The amount of the residue drawn out per hour was 96 grams, and the amount of the distillate drawn out per hour was 111 grams. The composition of the residue was analyzed. The residue was composed of 21.5 percent of phenyl valerate, 20.4 percent of methyl phenyl carbonate, 14.4 percent of diphenyl carbonate, 6.7 percent of dimethyl carbonate, 12.4 percent of methyl valerate, and 24.7 percent of phenol. The conversion of phenol was 60.0 percent, and the conversion of dimethyl carbonate was 71.5 percent.

[EXAMPLE 3]

A consecutive multiple reaction was carried out using the same reactive distillation equipment as that used in Example 1, under the same reaction conditions as those in Example 1, except that the amount of the raw material liquid containing phenol fed per hour was changed to 63 grams from 60 grams of Example 1, the amount of methyl valerate fed per hour was changed to 136 grams from 128 grams, and the amount of dimethyl carbonate fed per hour was changed to 18.7 grams from 18.6 grams.

The amount of the residue drawn out per hour was 115 grams, and the amount of the distillate drawn out per hour was 101 grams. The composition of the residue was analyzed. The residue was composed of 29.4 percent of phenyl valerate, 14.9 percent of methyl phenyl carbonate, 11.0 percent of diphenyl carbonate, 3.9 percent of dimethyl carbonate, 13.3 percent of methyl valerate, and 27.5 percent of phenol. The conversion of phenol was 58.5 percent, and the conversion of dimethyl carbonate was 80.0 percent.

INDUSTRIAL APPLICABILITY

Reactive distillation equipment of the present invention is applicable to a relatively complicated reaction composed of at least two steps of equilibrium reactions, i.e., a consecutive multiple reaction.

A reactive distillation method of the present invention is applicable to a relatively complicated reaction composed of at least two steps of equilibrium reactions, i.e., a consecutive multiple reaction, and enables efficient preparation of industrially useful carbonate esters. For example, diphenyl carbonate as a kind of the carbonate esters is used as a raw material of industrially useful polycarbonate.

What is claimed is:

1. A reactive distillation method for performing a reaction composed of at least two equilibrium reactions using a reactive distillation equipment having not less than three stages, comprising at least the steps of:

performing a first equilibrium reaction between two kinds of raw materials by feeding a raw material (a first raw material) having a higher boiling point between the two kinds of raw material to a first stage and feeding the other raw material (a second raw material) having a lower boiling point to a second stage lower than the first stage: and performing a second equilibrium reaction between a third raw material and a product having a boiling point higher than the first and second raw materials between products produced by the first equilibrium reaction by feeding the third material to a third stage lower than the second stage.

2. The reactive distillation method as set forth in claim 1, wherein a product having a lower boiling point between products produced by the second equilibrium reaction is a raw material of the first equilibrium reaction.

3. The reactive distillation method as set forth in claim 1, wherein the first equilibrium reaction is a transesterification reaction between a carboxylate ester represented by formula (1)

$$R^1COOR^2 \tag{1}$$

(wherein each of $R^1$ and $R^2$ independently represents an alkyl group, an alicyclic hydrocarbon group, or an aryl alkyl group) and an aromatic hydroxy compound of formula (2)

$$R^3OH \tag{2}$$

(wherein $R^3$ represents an aromatic group with or without a substituent), and the second equilibrium reaction is a transesterification reaction between a carboxylate ester represented by formula (3)

$$R^1COOR^3 \tag{3}$$

(wherein $R^1$ represents an alkyl group, an alicyclic hydrocarbon group, or an aryl alkyl group, and $R^3$ represents an aromatic group with or without a substituent) and a carbonate ester of formula (4)

$$R^4O-COOR^5 \tag{4}$$

(wherein each of $R^4$ and $R^5$ independently represents an alkyl group, an alicyclic hydrocarbon group, or an aryl alkyl group), the carboxylate ester of formula (3) being produced by the transesterification reaction between the carboxylate ester of formula (1) and the aromatic hydroxy compound of formula (2).

4. The reactive distillation method as set forth in claim 1, wherein the boiling point of the third raw material is lower than the boiling points of the first and second raw materials.

5. The reactive distillation method as set forth in claim 1, wherein the first equilibrium reaction is performed at a temperature and a pressure which have been adjusted so that products having a boiling point higher than the boiling points of the first and second raw materials between the product produced by the first equilibrium reaction are separable from the first and second raw materials based on differences in boiling point.

6. The reactive distillation method as set forth in claim 1, wherein the first equilibrium reaction is performed at a temperature and a pressure which have been adjusted so that products having a boiling point lower than the boiling points of the first and second raw materials between the products produced by the first equilibrium reaction is separated and removed based on differences in boiling point, and the first equilibrium reaction is promoted.

7. The reactive distillation method as set forth in claim 1, wherein the second equilibrium reaction is performed at a temperature and a pressure which have been adjusted so that a product having a higher boiling point between the products produced by the second equilibrium reaction is separated as a target product based on differences in boiling point, and removed from a reaction separator.

8. The reactive distillation method as set forth in claim 1, wherein the second equilibrium reaction is performed at a temperature and a pressure which have been adjusted so that a product having a lower boiling point between the products produced by the second equilibrium reaction is separated from a second equilibrium reaction system based on differences in boiling point, and the second equilibrium reaction is promoted.

9. The reactive distillation method as set forth in claim 1, wherein a target product produced by the second equilibrium reaction is carbonate diester.

10. A reactive distillation apparatus having not less than three states for performing a reaction composed of at least two equilibrium reactions, the apparatus comprising:

a first feed section for feeding a first raw material having a higher boiling point between two kinds of raw materials for performing a first equilibrium reaction;

a second feed section for feeding second raw material having a lower boiling point than the first raw material;

a third feed section for feeding a third raw material which executes a second equilibrium reaction with a product having a boiling point higher than the first and second raw materials between products produced by the first equilibrium reaction, the first, second and third feed sections placed on different stages in this order from a top of a column downward; and a reboiler which removes bottom liquid from a bottom of the column, heats the withdrawn bottom liquid and returns the bottom liquid to the bottom of the column.

11. The reactive distillation equipment as set forth in claim 10, further comprising a stage having no feed section, between the two stages provided with the feed sections.

12. The reactive distillation apparatus of claim 10, further comprising a condenser which condenses distillate fed from the top of the column, liquidizes the distillate, and returns the distillate to the top of the column.

* * * * *